United States Patent
Zhou et al.

(10) Patent No.: US 7,824,539 B2
(45) Date of Patent: Nov. 2, 2010

(54) IONIC BASED SENSING FOR IDENTIFYING GENOMIC SEQUENCE VARIATIONS AND DETECTING MISMATCH BASE PAIRS, SUCH AS SINGLE NUCLEOTIDE POLYMORPHISMS

(75) Inventors: Yanxiu Zhou, West Hartford, CT (US); Bin Yu, West Hardford, CT (US); Kalle Levon, Brooklyn, NY (US)

(73) Assignee: Polytechnic Institute of New York University, Brooklyn, NY (US)

( * ) Notice: Subject to any disclaimer, the term of this patent is extended or adjusted under 35 U.S.C. 154(b) by 1536 days.

(21) Appl. No.: 11/090,944

(22) Filed: Mar. 25, 2005

(65) Prior Publication Data

US 2008/0197025 A1    Aug. 21, 2008

Related U.S. Application Data

(60) Provisional application No. 60/556,231, filed on Mar. 25, 2004.

(51) Int. Cl.
G01N 27/26 (2006.01)
(52) U.S. Cl. .............. 205/792; 205/777.5; 436/531; 422/82.03; 435/287.2
(58) Field of Classification Search ........... 436/518, 436/501, 527, 531; 422/82.01, 82.02, 82.03, 422/82.06; 205/777.5, 792; 435/6, 287.2
See application file for complete search history.

(56) References Cited

U.S. PATENT DOCUMENTS 5,491,097 A    2/1996   Ribi et al.

2002/0090649 A1    7/2002   Chan et al.
2003/0157527 A1    8/2003   Lastrucci
2005/0230271 A1*  10/2005   Levon et al. ............. 205/789

OTHER PUBLICATIONS

Kim, D.-S., et al. "Fabrication and Characterization of a Field Effect Transistor-Type Charge Sensor for Detecting Deoxyribonucleic Acid Sequence", Japanese Journal of Applied Physics, Part I, vol. 42, No. 6B, Jun. 2003, p. 4111-4115.*

(Continued)

Primary Examiner—Nam X Nguyen
Assistant Examiner—J. Christopher Ball
(74) Attorney, Agent, or Firm—Straub & Pokotylo; John C. Pokotylo

(57) ABSTRACT

Ionic interactions are monitored to detect hybridization. The measurement may be done measuring the potential change in the solution with the ion sensitive electrode (which may be the conducting polymer (e.g., polyaniline) itself), without applying any external energy during the binding. The double helix formation during the complimentary hybridization makes this electrode act as an ion selective electrode—the nucleotide hydrogen bonding is specific and thus monitoring the ionic phosphate group addition becomes selective. Polyaniline on the surface of nylon film forms a positively charged polymer film. Thiol linkage can be utilized for polyaniline modification and thiol-modified single strand oligonucleotide chains can be added to polyaniline. The sensitivity is because the double helix formation during the complimentary hybridization makes this electrode act as an ion selective electrode as the nucleotide hydrogen bonding is specific and thus monitoring the ionic phosphate group addition becomes selective.

23 Claims, 11 Drawing Sheets

OTHER PUBLICATIONS

Souteyrand, E., et al. "Direction Detection of the Hybridization of Synthetic Homo-Oligomer DNA Sequences by Field Effect", Journal of Physical Chemistry, B, vol. 101, No. 15, no month given, 1997, p. 2980-2985.*

Fritz, J., et al. "Electronic Detection of DNA by its Intrinsic Molecular Charge", Proceedings of the National Academy of Science, USA, vol. 99, No. 22, Oct. 2002, p. 14142-14146.*

Pouthas, F. et al. "DNA Detection on Transistor Arrays Following Mutation-Specific Enzymatic Amplification", Applied Physics Letters, vol. 84, No. 9, Mar. 1, 2004, p. 1594-1596.*

Janata, J. "Twenty Years of Ion-Selective Field-effect Transistors", Analyst, vol. 119, Nov. 1994, p. 2275-2278.*

Campanella, L., et al. "Sensitive Memberane ISFETs for Nitrate Analysis in Waters", Sensors and Actuators, vol. 26-27, 1995, p. 329-335.*

Campanella, L., et al. "New Polymeric Membrane ISFETs and ISEs Responsive to Cationic Surfactants", 8th International Conference on Solid-State Sensors and Actuators and Eurosensors IX, Jun. 1995, p. 944-947.*

* cited by examiner

Potentiometric Response of Sensor to Solution of Various Conc. Of DNA (Set 1) (14 mer)

(A) Calibration curves for the potentiometric responses of the (●) cDNA and (♦) ncDNA on sensor at 0.5 M NaCl – 50 mM PBS hybridization buffer (pH 7.0). (B) linear results

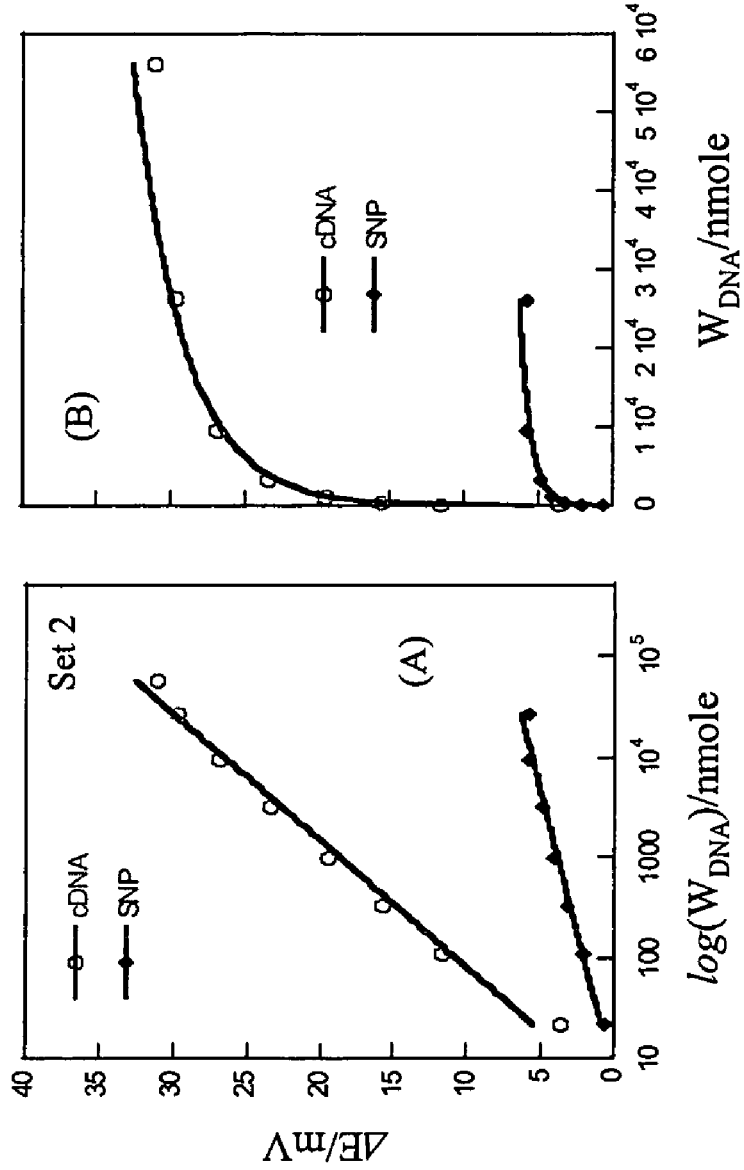
(A) Calibration curves for the potentiometric responses of the (○) cDNA and (♦) one-base mismatch on sensor at 0.5 M NaCl ~ 50 mM PBS hybridization buffer (pH 7.0). (B) linear results

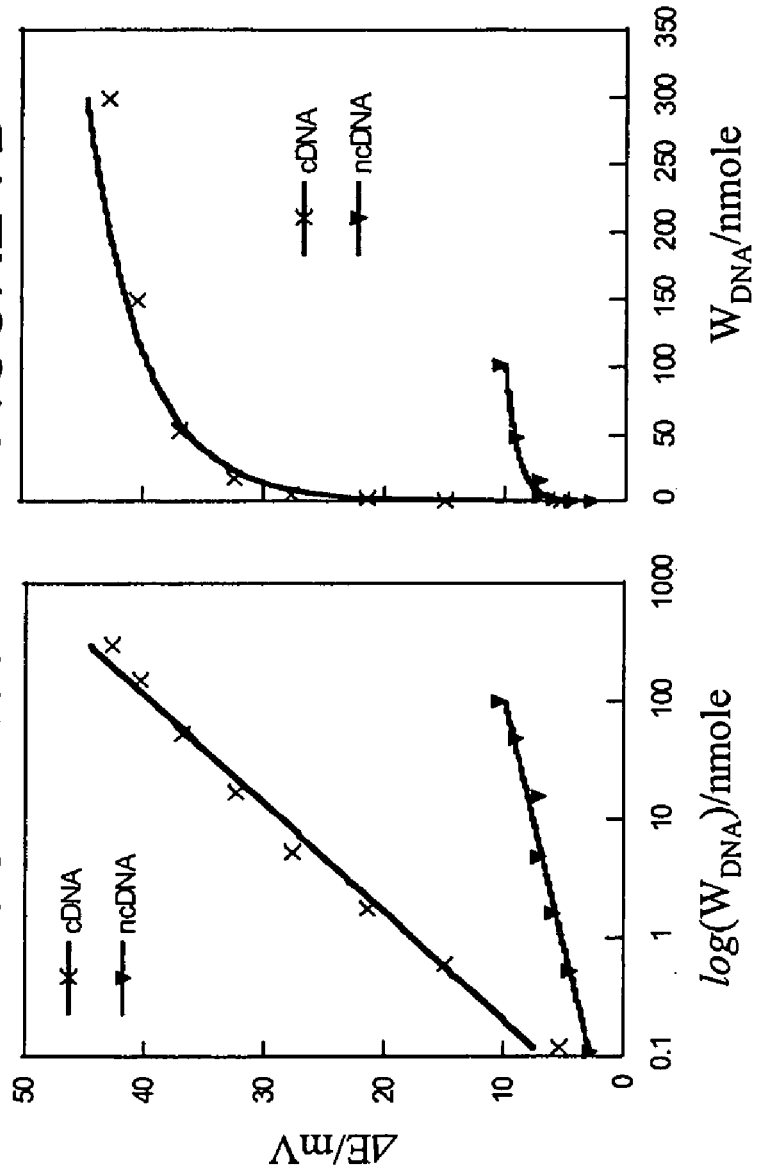
(A) Calibration curves for the potentiometric responses of the ODN on sensor at 0.5 M NaCl – 50 mM PBS hybridization buffer (pH 7.0).

Potentiometric Response of Sensor
to Solution of Various Conc. Of DNA (Set 1)

(A) Calibration curves for the potentiometric responses of DNA (Set 1) on sensor fabricated by Physical Adsorption at 0.5 M NaCl – 50 mM PBS hybridization buffer (pH 7.0). (B) linear results

SEQUENCE LISTING

```
<160> NUMBER OF SEQ ID NOS: 12

<210> SEQ ID NO 1
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1
cctaagaggg agtg                                                      14

<210> SEQ ID NO 2
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 2
cactccctct tagg                                                    14

<210> SEQ ID NO 3
<211> LENGTH: 15
<212> TYPE: DNA
<213> ORGANISM: Artificial Sequence
<220> FEATURE:
<223> OTHER INFORMATION: Synthetic Construct

<400> SEQUENCE: 3
ggtgatagaa gtatc                                                   15

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
tcaatctcgg gaatctcaat gttag                                        25

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
ctaacattga gattcccgag attga                                        25

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
ctaacattga gattcacgag attga                                        25

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
tgtgacaacc acatcactgt                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
acagtgatgt ggttgtcaca                                              20

<210> SEQ ID NO 9
<211> LENGTH: 20
```

-continued

```
<212> TYPE: DNA
<213> ORGANISM: Artificial Sequence
<220> FEATURE:
<223> OTHER INFORMATION: Synthetic Construct

<400> SEQUENCE: 9
tgtgacaacc acatcactga                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tcagtgatgt ggttgtcaca                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
agtctgatga ggtactgtga                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
gcaacgaccc ttgacacacg                                               20
```

IONIC BASED SENSING FOR IDENTIFYING GENOMIC SEQUENCE VARIATIONS AND DETECTING MISMATCH BASE PAIRS, SUCH AS SINGLE NUCLEOTIDE POLYMORPHISMS

§0.1 CROSS REFERENCE TO RELATED APPLICATIONS

This application claims the benefit of U.S. Provisional Patent Application Ser. Nos. 60/556,231 (incorporated herein by reference), titled "IONIC BASED SENSING FOR IDENTIFYING GENOMIC SEQUENCE VARIATIONS AND DETECTING MISMATCH BASE PAIRS, SUCH AS SINGLE NUCLEOTIDE POLYMORPHISMS," filed on Mar. 25, 2004.

§0.2 GOVERNMENT FUNDING

This invention was made with Government support and the Government has certain rights in the invention as provided for by contract number 0660076225 awarded by DARPA.

§0.3 SEQUENCE LISTING

This application incorporates by reference a sequence listing on two CD-Rs having a machine format of IBM-PC and an operating system of MS-Windows-XP. Each CD-R contains a text file, titled "Sequence Listing", created on Dec. 20, 2007, and 3KB in size. The Sequence Listing adds no new matter.

§1. BACKGROUND

§1.1 Field of the Invention

This invention relates generally to the field of sensors and in particular to biosensors specific to nucleotide sequences.

§1.2 Background Information

Diagnostics for DNA sequence variations have increasing importance for revealing genetic markers in the exploration of diseases and traits with complex inheritance patterns and strong environmental interactions.

The use of potentiometric ion electrodes (ISEs) represents one of the oldest classes of chemical sensors. The selectivities of these potentiometric ion sensors were quantitatively related to equilibria at the interface between the sample and the electrode membrane by Bakker et al. (See, e.g., Eric Bakker, Emo Pretsch, Philippe Buhlmann, Anal. Chem. 2000 72 1127-1133.)

Melnikov, Sergeyev and Yoshikawa applied a potentiometric study of the binding equilibrium of cationic surfactants with DNA. The calibration curve consisted of the titration curve with the surfactants and the experiment itself followed the addition of DNA to the surfactant solution. The deviation from the calibration was believed to be due to the decrease in the free surfactant concentration caused by the binding to the oppositely charged DNA macro-ions. (See, e.g., S. M. Melnikov, V. G. Sergeyev, K. Yoshikawa, "Transition of Double-Stranded DNA Chains between Random Coil and Compact Globule States Induced by Cooperative Binding of Cationic Surfactant," JACS, 1995, 117, 9951-9956.)

McConnell et. al. used a silicon-based device (a microphysiometer) to measure the rate of protein excretion from cells during binding of ligands for specific membrane receptors. Because of the use of specific ligands, microphysiometer measures selectively the acidic products of energy metabolism or other physiological changes from changes in intracellular pH. (See, e.g., H. M. McConnell, J. C. Owicki, J. W. Parce, D. L. Miller, G. T. Baxter, H. G. Wada, S. Pitchford Science 1992 257 1906-1912.)

The potentiality of such an ion sensitive detection lies in the development of ion sensitive field effect transistors and especially using binding on surfaces of nanoscale elements such as single wall carbon nano tubes, because the binding can lead to changes in the number of carriers in the nanometer diameter structure (and not only in the surface conductivity as in planar devices) and thus increase the sensitivity to single-molecule level. (See, e.g., Y. Cui, Q. Wei, H. Park, C. M. Lieber, Science 2001 293.)

It would be useful to have an improved sensor and sensing method and system for detecting the presence and/or concentration of nucleotide strands. It would be useful if such a sensor and sensing method and system did not require the application of a voltage from an external source.

§2. SUMMARY OF THE INVENTION

Methods, apparatus and compositions of matter consistent with the present invention use, or may be used with, ionic-based sensors for identifying genomic sequence variations and detecting mismatch base pairs, such as single nucleotide polymorphisms (SNPs) for example. A method for detecting or measuring nucleotide strand hybridization in a manner consistent with the present invention may (a) provide an ion sensitive electrode in solution, and (b) determine a potential change in the solution without applying any external energy (e.g., voltage from an external source) during the hybridization.

In at least some embodiments consistent with the present invention, the ion sensitive electrode comprises an electrically conducting polymer (which may be ionically charged in its doped form). The electrically conducting polymer may be polyaniline.

In at least some embodiments consistent with the present invention, the ion sensitive electrode may include probes comprising nucleotide strands. In such embodiments, it may be determined whether or not the solution includes complementary nucleotide strands using the determined potential change. In at least some embodiments consistent with the present invention, this determination can distinguish a single nucleotide polymorphism.

§3. BRIEF DESCRIPTION OF THE DRAWINGS

FIGS. 5A and 5B illustrate potentiometric responses of the first exemplary sensor for complementary and single base mismatch DNA for the second set of oligonucleotides.

FIGS. 7A and 7B illustrate potentiometric responses of the second exemplary sensor for complementary and non-complementary DNA for the first set of oligonucleotides.

§4. DETAILED DESCRIPTION

The following description is presented to enable one skilled in the art to make and use our invention, and is provided in the context of further particular embodiments and methods. The present invention is not limited to the particular embodiments and methods described.

§4.1 Definitions

"ODN" means oligonucleotide.

An "SNP" is a nucleotide (e.g., DNA) sequence variation, occurring when a single nucleotide: adenine (A), thymine (T), cytosine (C) or guanine (G)—in the sequence is altered.

The prefix "c" means complementary. Thus, for example, cDNA means complementary DNA.

The prefix "nc" means non-complementary.

"Conductive" and "conducting" materials are intended to include "semi-conductive" materials.

"SS" means single stranded.

§4.2 Exemplary Sensors

The following sensors may exploit the fact that given nucleotide strands immobilized on an conductive (or semi-conductive) substrate will have a binding energy with a complementary strand that is greater than the binding energy of a non-complementary strand (e.g., a mutated strand, an SNP, etc.).

Figure 1:
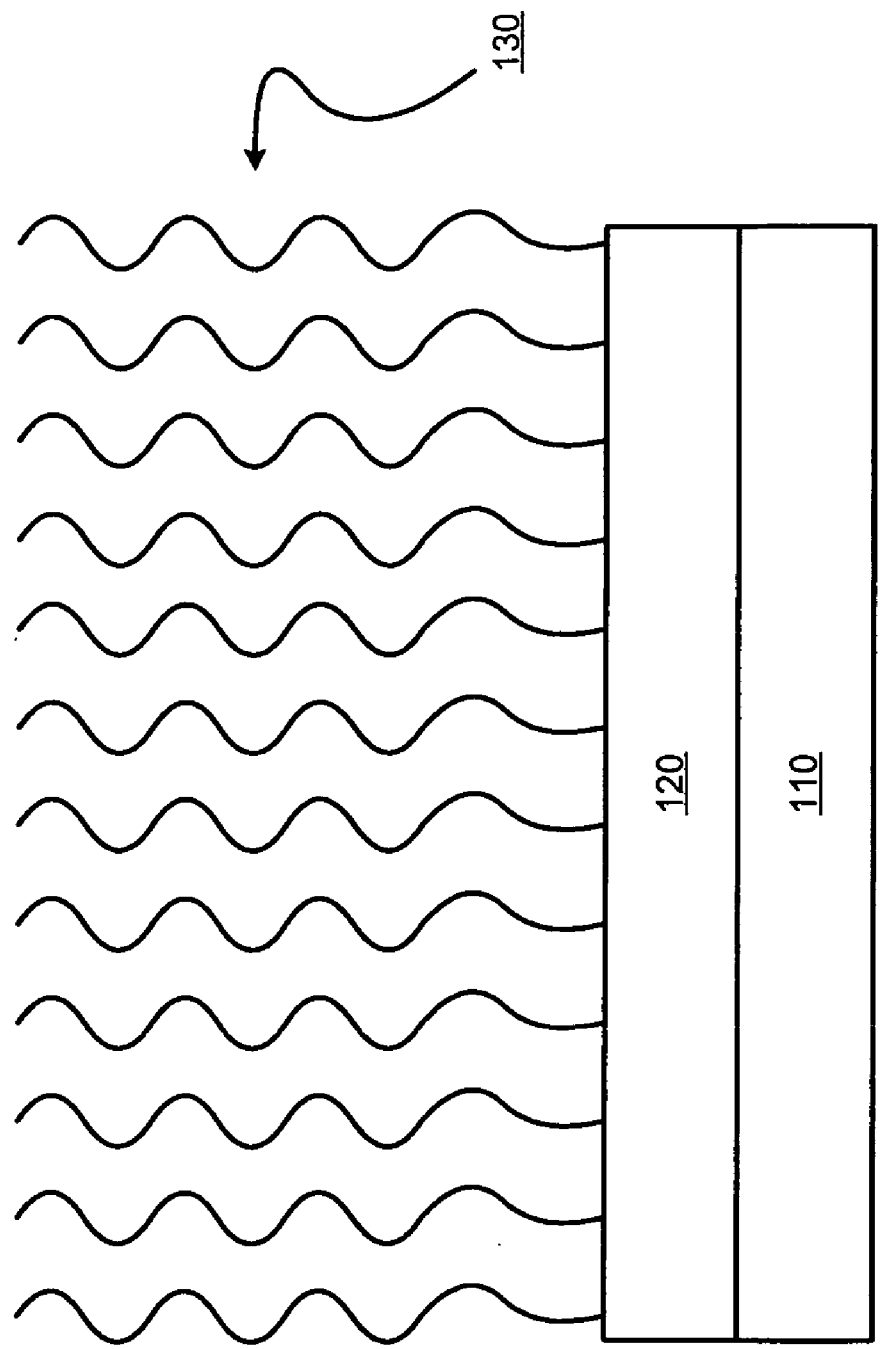
FIG. 1 is a diagram illustrating a sensor consistent with the present invention.

FIG. 1 is a diagram of an exemplary sensor. Although this diagram is provided as a two-dimensional cross section, it should be understood that the elements are three-dimensional. The sensor includes an electrode substrate 110, a conductive immobilization layer 120, and probes 130 immobilized onto the layer 120.

In one embodiment, the electrode 110 is ITO, the conductive immobilization layer 120 is a three dimensional network of polyaniline and the probes 130 are ODNs. Specific ODNs discussed in detail below include Set 1:

```
probe:              5'-CCT/AAG/AGG/GAG//TG-3'
complementary:      5'-CAC/TCC/CTC/TTA//GG-3'
non-complementary:  5'-GGT/GAT/AGA/AGT//ATC-3'
```

Set 2:

```
probe:
5'-TCA/ATC/TCG/GGA/ATC/TCA/ATG/TTA/G-3 complementary:
5'-CTA/ACA/TTG/AGA/TTC/CCG/AGA/TTG/A-3' one-base mismatch
5'-CTA/ACA/TTG/AGA/TTC/ACG/AGA/TTG/A-3' non-complementary:
5'-GGT/GAT/AGA/AGT/ATC-3
```

Set 3:

```
probe (2-1):   5'-TGT/GAC/AAC/CAC/ATC/ACT/GT-3'
cDNA           5'-ACA/GTG/ATG/TGG/TTG/TCA/CA-3'
probe (1-1)    5'-TGT/GAC/AAC/CAC/ATC/ACT/GA-3'
cDNA           5'-TCA/GTG/ATG/TGG/TTG/TCA/CA-3'
50% mismatch   5'-AGT/CTG/ATG/AGG/TAC/TGT/GA-3'
100% mismatch  5'-GCA/ACG/ACC/CTT/GAC/ACA/CG-3'
```

Alternative electrodes 110 include, for example, platinum, glassy carbon, a semi-conducting metal oxide, etc. In at least one embodiment consistent with the present invention, the layer 120 itself acts as the electrode, in which case a separate electrode layer 110 is not required. If the layer 120 lacks sufficient mechanical strength, it may be incorporated on or with another material (e.g., nylon, a semiconducting metal oxide, etc., but need not be metal oxide).

Alternative conductive immobilization layers 120 are possible. For example, polyaniline (PANI) is a conducting polymer. The present inventors believe that other conductive polymers may be used for the conductive immobilization layer 120. Examples of common classes of organic conductive polymers include poly(acetylene)s, poly(pyrrole)s, poly(thiophene)s, poly(aniline)s, poly(p-phenyliene sulfide), poly(para-phenylene vinylene)s, polyacetylene (PA), Polypyrrole (PPy), and Polythiophene (PT).

Alternative probes 130 include, for example, other ODNs (preferably between 6 and 75 nucleotides), polymerase chain reaction ("PCR") products, genomic DNAs, bacterial artificial chromosomes ("BACs"), plasmids, etc.

§4.3 Exemplary Techniques for Fabricating Sensors

The probes 130 can be immobilized on the polymer 120 by any covalent immobilization method (such as, for example, thiol addition or ester or amide bond formation, etc.), or by any non-covalent immobilization method (such as, for example, ink jet printing, layer-by-layer deposition method, etc.). In a first exemplary embodiment consistent with the present invention, polyaniline-based sulfhydryl-linkage immobilization in under CV is used to immobilize the probes 130 on the polymer 120. In a second exemplary embodiment consistent with the present invention, polyaniline-based sulfhydryl-linkage immobilization via absorption is used to immobilize the probes 130 on the polymer 120. In a third exemplary embodiment consistent with the present invention, the probes 130 are immobilized on the electrode via physical absorption. In a fourth exemplary embodiment consistent with the present invention, the probes 130 are immobilized on the electrode via electrochemical activation. In a fifth exemplary embodiment consistent with the present invention, the probes 130 are immobilized using polysiloxane monolayer immobilization ("PMI"). PMI is described in U.S. patent application Ser. No. U.S. patent application Ser. No.: 10/888, 342 (incorporated herein by reference), titled "BIOSENSOR AND METHOD OF MAKING SAME", filed on Jul. 9, 2004, and listing Yanxiu Zhou, Bin Yu and Kalle Levon as inventors.

§4.4 Exemplary Sensors Fabricated Using Various Exemplary Techniques Consistent with the Present Invnetion, as Well as Characteristics Thereof In the following experimental examples, oligonucleotide samples were ordered from Genemed Synthesis, Inc.:

Set 1:

```
probe:            5'-CCT/AAG/AGG/GAG//TG-3' complementary:    5'-CAC/TCC/CTC/TTA//GG-3' non-complementary: 5'-GGT/GAT/AGA/AGT//ATC-3'
```

Set 2:

```
probe:
5'-TCA/ATC/TCG/GGA/ATC/TCA/ATG/TTA/G-3 complementary:
5'-CTA/ACA/TTG/AGA/TTC/CCG/AGA/TTG/A-3' one-base mismatch
5'-CTA/ACA/TTG/AGA/TTC/ACG/AGA/TTG/A-3' non-complementary:
5'-GGT/GAT/AGA/AGT/ATC-3
```

Set 3:

```
probe (2-1):     5'-TGT/GAC/AAC/CAC/ATC/ACT/GT-3' cDNA             5'-ACA/GTG/ATG/TGG/TTG/TCA/CA-3' probe (1-1)     5'-TGT/GAC/AAC/CAC/ATC/ACT/GA-3' cDNA             5'-TCA/GTG/ATG/TGG/TTG/TCA/CA-3'

50% mismatch   5'-AGT/CTG/ATG/AGG/TAC/TGT/GA-3'

100% mismatch   5'-GCA/ACG/ACC/CTT/GAC/ACA/CG-3'
```

For the hybridization assay, ODN were dissolved in a stock PBS hybridization buffer (0.5 M NaCl, 50 mM $PO_4^{-n}$, pH 7.0). Assays were done using solution temperatures of 37° C.

Figure 2:
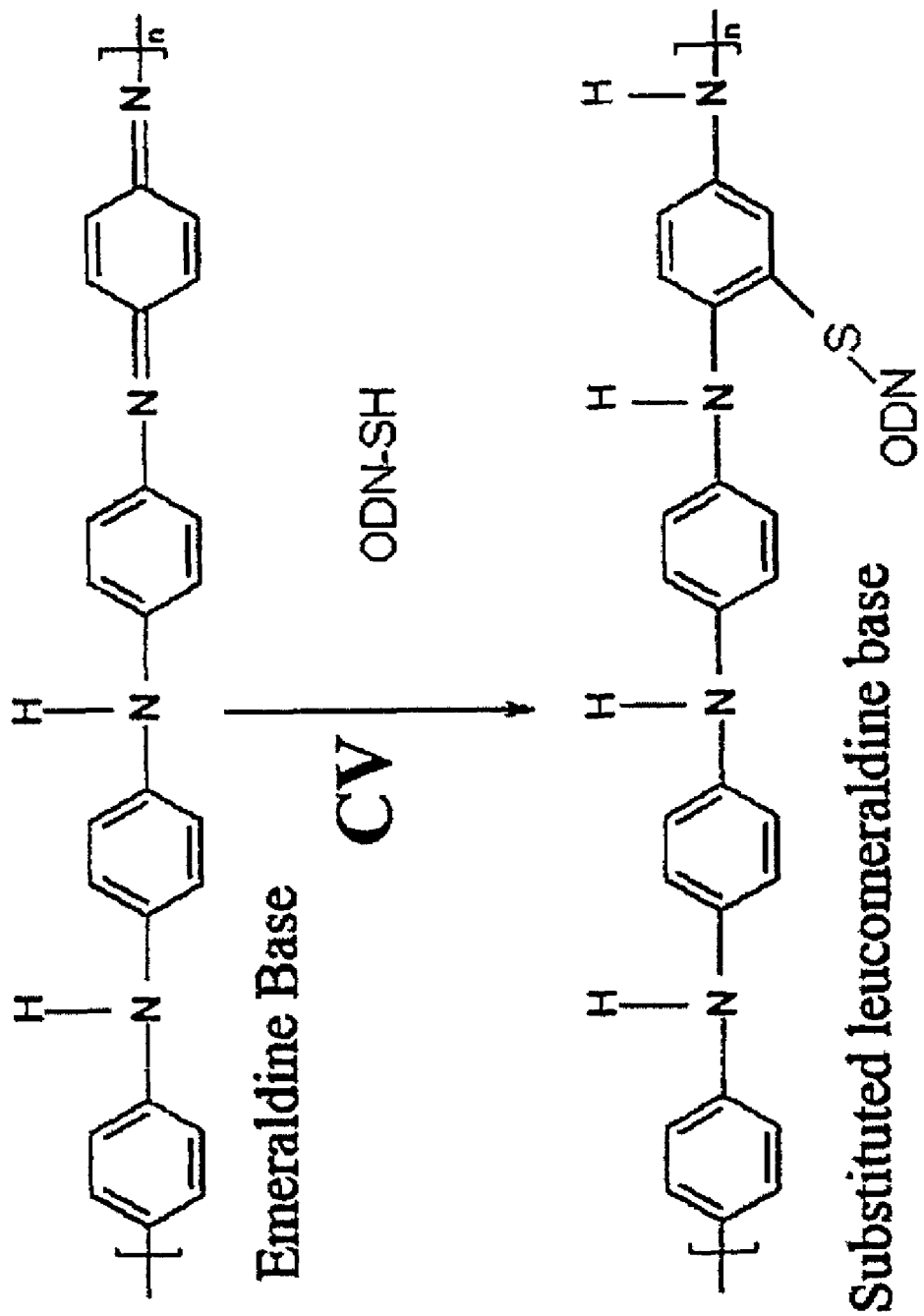
FIG. 2 illustrates an immobilization process used to fabricate a first exemplary sensor.

§4.4.1 Exemplary Sensor Fabricated Using a First Technique and Characteristics Thereof In a first exemplary embodiment consistent with the present invention, polyaniline-based sulfhydryl-linkage immobilization in under CV is used to immobilize the probes 130 on the polymer 120. More specifically, ODN probes were attached on the PANi film by cyclic voltammetry (EG&G VersaStat II) with the three-electrode system consisted of a Ag/AgCl reference electrode, platinum wire as an auxiliary electrode and a Pt, glassy carbon electrode or ITO glass as a working electrode. FIG. 2 illustrates this immobilization process. This is an example of covalently attached probes.

Figure 3:
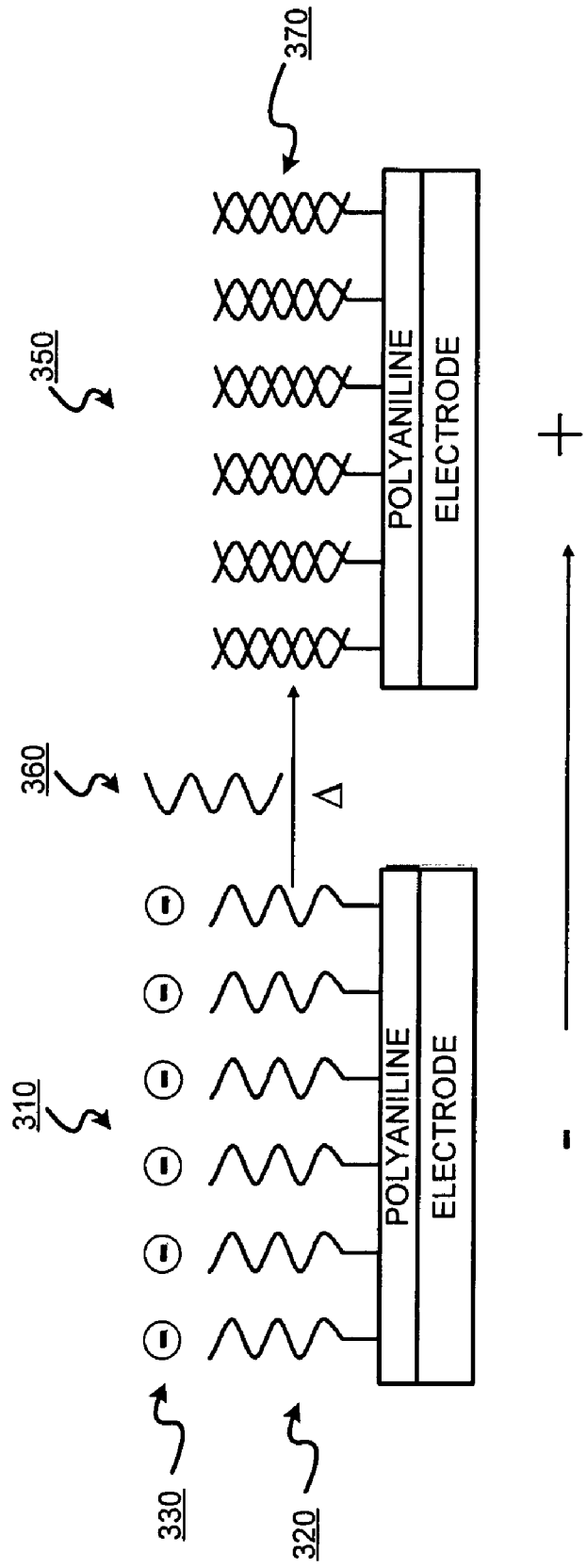
FIG. 3 illustrates how a sensor consistent with the present invention can detect hybridization of the probes and complementary DNA.

FIG. 3 illustrates how such a sensor can detect hybridization of the probes and complementary DNA. The potential change in the solution is measured with the ion sensitive electrode (e.g., polyaniline) without applying any external energy (e.g., external charge from an external voltage source) during the hybridization. As shown at a first time 310, probes 320 have a negative charge 330. Complementary DNA is added 360. Then, at a second time 350, the double helix formation 370 during the complimentary hybridization makes this electrode act as an ion selective electrode as the nucleotide hydrogen bonding is specific and thus monitoring the ionic phosphate group addition becomes selective.

Figures 4A, 4B:
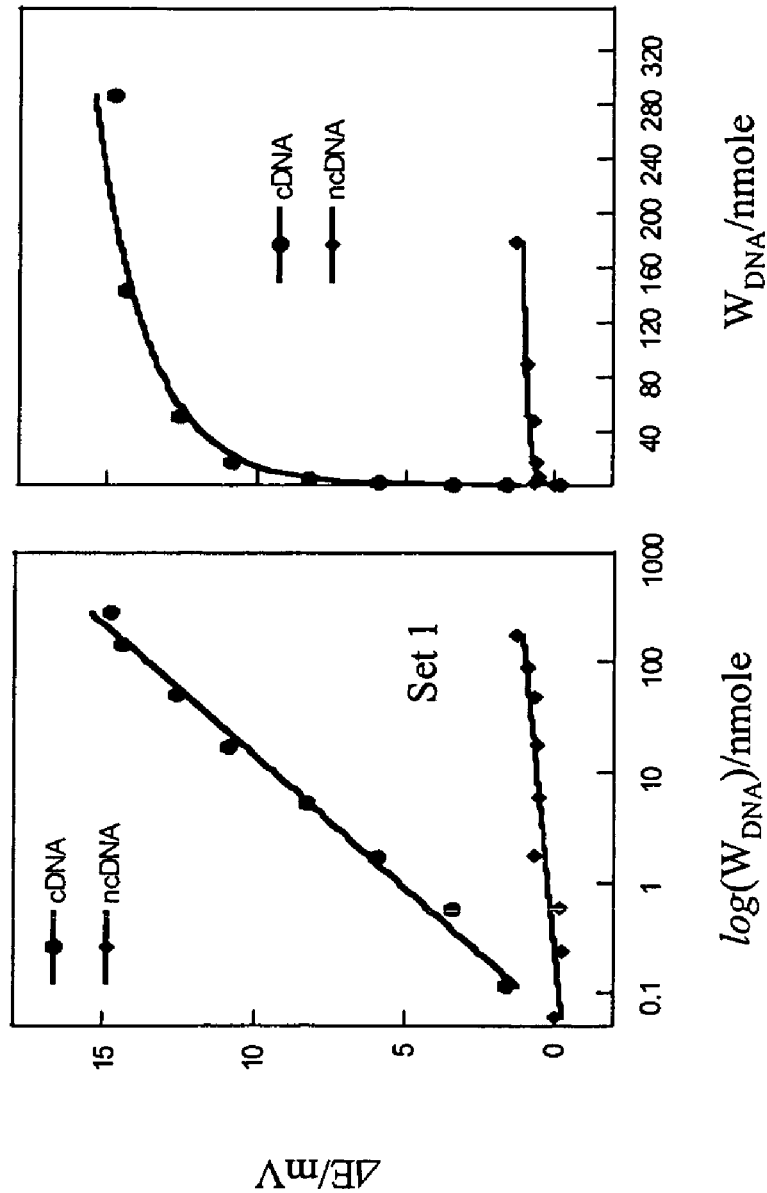
FIGS. 4A and 4B illustrate potentiometric responses of the first exemplary sensor for complementary and non-complementary DNA for the first set of oligonucleotides.

The potentials of the sensor were measured against Ag|AgCl reference electrode with an Orion 920A Potentiometer. FIGS. 4A and 4B illustrate potentiometric responses of the first exemplary sensor for complementary and non-complementary DNA for the first set of oligonucleotides. As shown, for ncDNA no hybridization occurs. The slight increase may originate from ncDNA's non-specific binding with the cationic polyaniline surface. This effect may be reduced by saturating the surface with probes. When cDNA binds, an increase in potential indicates the occurrence of hybridization.

FIGS. 5A and 5B illustrate potentiometric responses of the first exemplary sensor for complementary and single base mismatch DNA for the second set of oligonucleotides. The single mismatch in set 2 is in the middle of the target.

Figure 6:
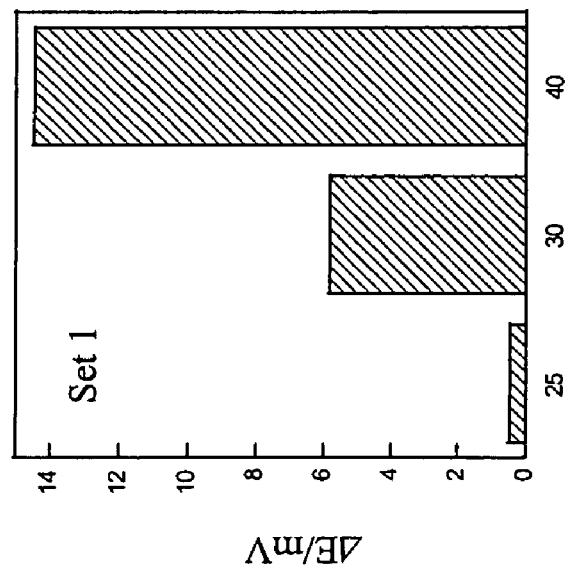
FIG. 6 shows the influence of hybridization temperature on the difference in potential differences between complementary and non-complementary nucleotide strands

FIG. 6 shows the influence of hybridization temperature on the difference in potential differences between complementary and non-complementary nucleotide strands.

§4.4.2 Exemplary Sensor Fabricated Using a Second Technique and Characteristics Thereof In a second exemplary embodiment consistent with the present invention, polyaniline-based sulfhydryl-linkage immobilization via absorption is used to immobilize the probes 130 on the polymer 120. This is a non-covalent—just a physical adsorption process. As shown below, it can detect hybridization with complementary DNA as well.

The potentials of the sensor were measured against Ag|AgCl reference electrode with an Orion 920A Potentiometer. FIGS. 7A and 7B illustrate potentiometric responses of the second exemplary sensor for complementary and non-complementary DNA for the first set of oligonucleotides. The attachment of ODN Probe has a thiol group so the nucleophile will like the basic nitrogen in polyaniline and bring DNA close to it (adsorption)

§4.4.3 Exemplary Sensor Fabricated Using a Third Technique and Characteristics Thereof In a third exemplary embodiment consistent with the present invention, the probes 130 are immobilized via physical absorption. The potential change in the solution is measured with the ion sensitive electrode (e.g., polyaniline) without applying any external energy during the hybridization. Double helix formation during the complimentary hybridization makes this electrode act as an ion selective electrode as the nucleotide hydrogen bonding is specific. Thus monitoring the ionic phosphate group addition becomes selective.

Figure 8A:
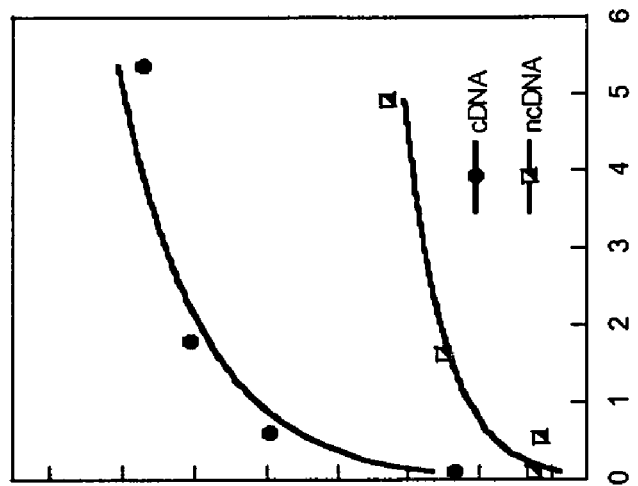
FIGS. 8A and 8B illustrate potentiometric responses of the third exemplary sensor for complementary and non-complementary DNA for the first set of oligonucleotides.
Figure 8B:
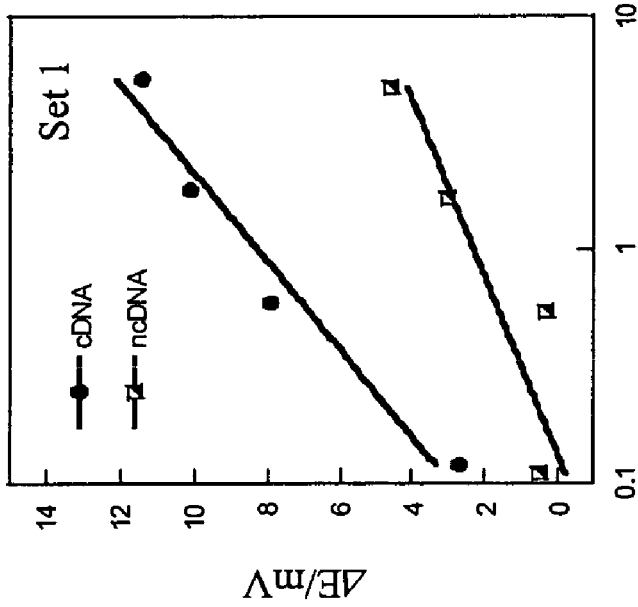

The potentials of the sensor were measured against Ag|AgCl reference electrode with an Orion 920A Potentiometer. FIGS. 8A and 8B illustrate potentiometric responses of the third exemplary sensor for complementary and non-complementary DNA for the first set of oligonucleotides. This has no thiol group—only ccDNA or ncDNA.

Figure 9:
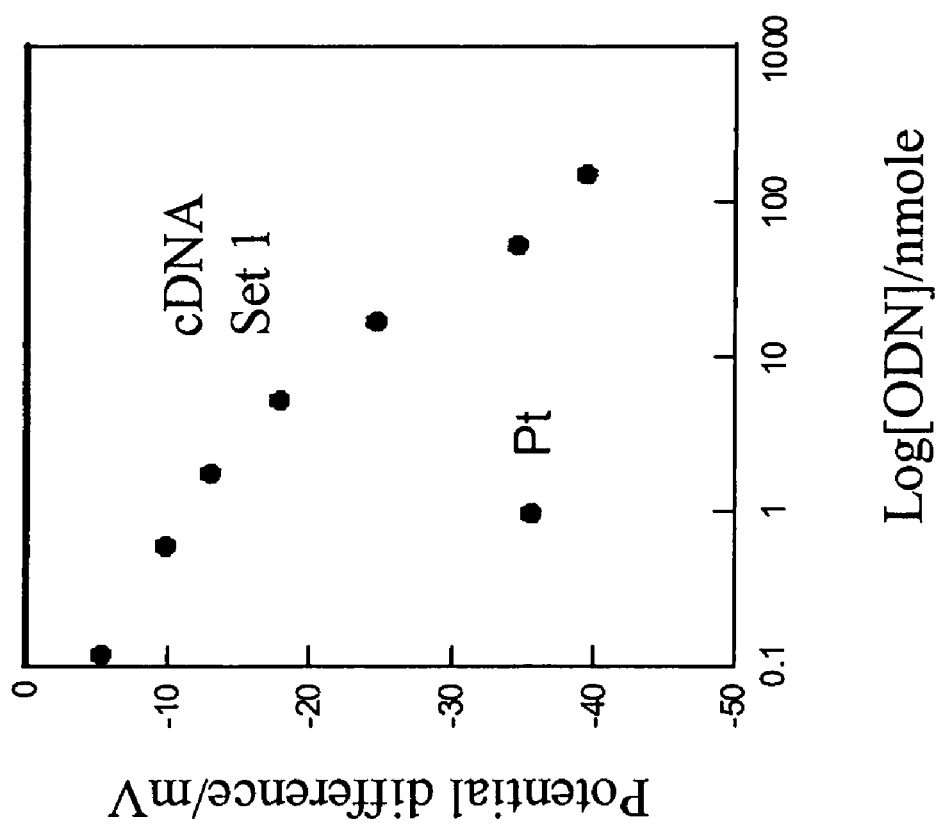
FIG. 9 illustrates the response of the ITO electrode to complementary DNA.

FIG. 9 illustrates the response of a Pt electrode having probes immobilized thereon, to complementary DNA. FIG. 9 provides an example of the ionic characteristics of oligonucleotide with the addition of ODN to a solution monitored with a platinum (inert) electrode showing the increase of anionic phosphate groups in the reaction vessel.

Figure 11:
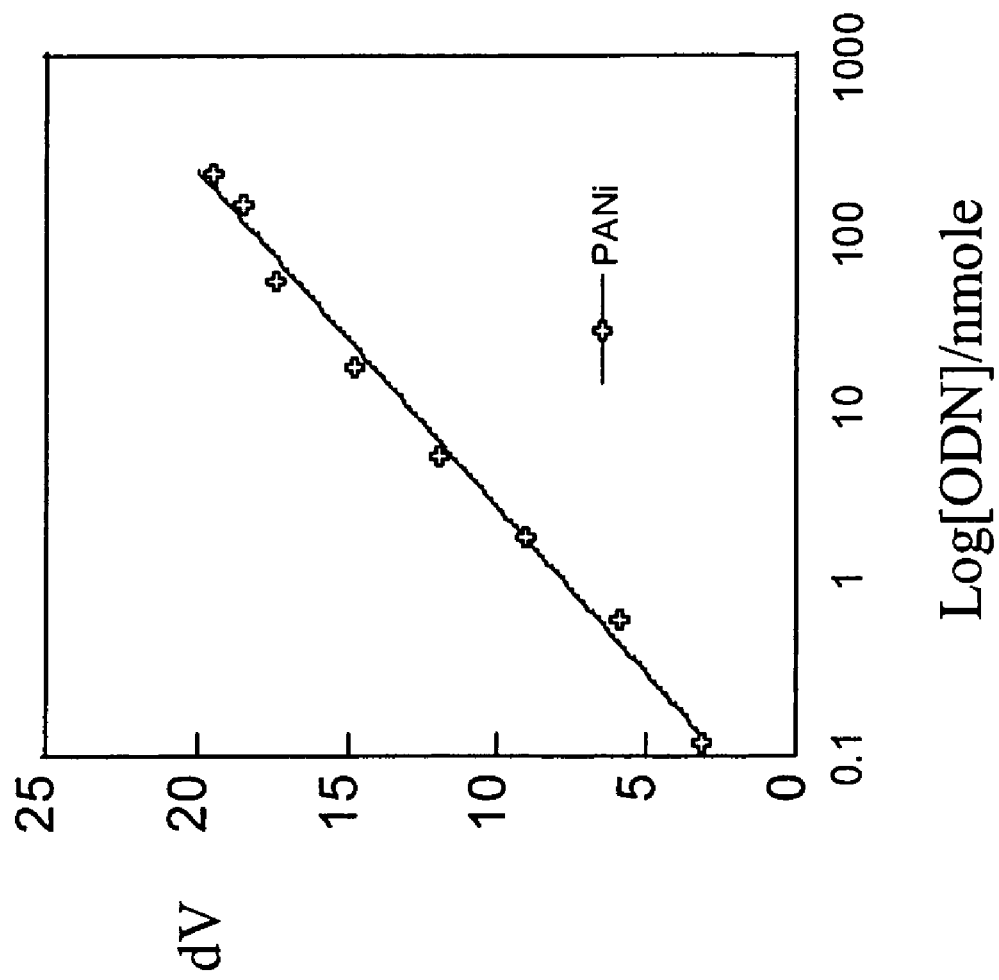
FIG. 11 illustrates a potential response.

FIG. 11 illustrates the a potential response of polyaniline. In this case, polyaniline being a positively charged surface, the anionic phosphate groups may complex with the surface charges releasing the counter ion pairs for entropic reasons. The counter ion concentration in the solution as well as the dielectric nature of the solvent/solution may influence the potential difference in addition to the ionic surface binding.

§4.5 Alternatives and Refinements

Alternative electrodes 110 include, for example, platinum, glassy carbon, a semi-conducting metal oxide, etc. In at least one embodiment consistent with the present invention, the layer 120 itself acts as the electrode, in which case a separate electrode layer 110 is not required. If the layer 120 lacks sufficient mechanical strength, it may be incorporated on or with another material (e.g., nylon). Polyaniline may be provided on a substrate either by depositing it onto the substrate surface, or electrochemically polymerizing it to the substrate surface (or first aniline is immersed and then polymerized within the substrate).

Alternative conductive immobilization layers 120 are possible. For example, polyaniline (PANI) is a conducting polymer. The present inventors believe that other conductive polymers may be used for the conductive immobilization layer 120. Examples of common classes of organic conductive polymers include poly(acetylene)s, poly(pyrrole)s, poly(thiophene)s, poly(aniline)s, poly(p-phenyliene sulfide), poly(para-phenylene vinylene)s, polyacetylene (PA), Polypyrrole (PPy), and Polythiophene (PT) (any of the above modified or unmodified) or any conducting polymers which is charged in its doped form.

Alternative probes 130 include, for example, other ODNs (preferably between 6 and 75 nucleotides), polymerase chain reaction ("PCR") products, genomic DNAs, bacterial artificial chromosomes ("BACs"), plasmids, etc.

The potentiometer measurements may be provided to a processor, such as a personal computer, for analysis. The potentiometer measurements may be made without application of energy (e.g., voltage from an external source) to the electrodes.

§4.6 Conclusions

The inventors believe that the sensitivity of the foregoing sensors is due to the variation of the potential difference at the electrolyte-insulator interface which, in turn, is due to a change of the chemical composition of the analyte (e.g., phosphate group concentration changes during hybridization). An electric field when applied to silicon by means of the reference electrode, changes concentration of charge carriers in the surface charge region of the semiconductor. The two different models explaining chemical sensitivity of the potential drop at the electrolyte-insulator interface are the ion exchange and the adsorption of potential-determining ions. Though of scientific interest, the relative influences of each of these contributors does not need to be understood to practice the present invention.

Figure 10:
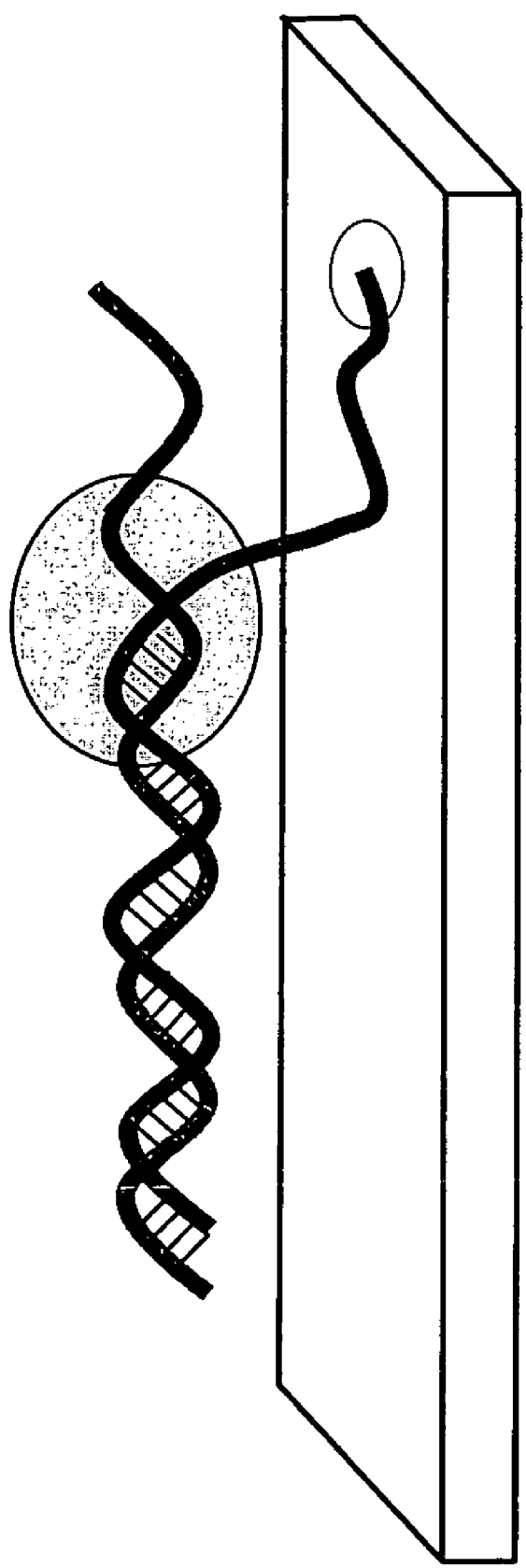
FIG. 10 illustrates the hybridization of a complementary nucleotide strand with a probe immobilized on a surface.

As can be appreciated from the foregoing, embodiments consistent with the present invention monitor ionic interactions to detect hybridization. The measurement is done measuring the potential change in the solution with the ion sensitive electrode (which may be the conducting polymer (e.g., polyaniline) itself), without applying any external energy during the binding. As illustrated in FIG. 10, the double helix formation during the complimentary hybridization makes this electrode act as an ion selective electrode—the nucleotide hydrogen bonding is specific and thus monitoring the ionic phosphate group addition becomes selective. Polyaniline on the surface of nylon film forms a positively charged polymer film. Thiol linkage can be utilized for polyaniline modification and thiol-modified single strand oligonucleotide chains can be added to polyaniline. The sensitivity is because the double helix formation during the complimentary hybridization makes this electrode act as an ion selective electrode as the nucleotide hydrogen bonding is specific and thus monitoring the ionic phosphate group addition becomes selective.

Although an ssDNA chain may be covalently immobilized on polyaniline surface, it is believed that the anionic phosphate chain forms an interpolymer complex with the cationic surface polymer due to the increasing entropy from the larger number of particles from the formation of counter ion pairs such as $Na^+$ and $Cl^-$. This ion activity during the interpolymer complex formation can be monitored using potentiometric approach. Polyaniline was used as the working electrode as earlier in the pH measurement. FIG. 18 shows the potentiometric change during the addition of the macromolecular ssDNA chain. The energetics of DNA hybridization are based on strong specific hydrogen bonding of A-T and G-C pairs and to the cooperative double helix formation and are cohesively stronger that the forces holding the interpolymer complex between polyaniline and ssDNA. For this reason, the hybridization can also be monitored via potential changes as the ion concentrations change essentially during the hybridization of the complementary single strand chains. The surface has to have overall neutrality to avoid ionic binding of a possible non-complimentary chain.

What is claimed is:

1. A method for detecting or measuring nucleotide strand hybridization comprising:
   a) providing an ion sensitive electrode in solution, wherein the ion sensitive electrode comprises an electrically conducting polymer and probes comprising nucleotide strands;
   b) determining a potential change in the solution without applying an externally sourced voltage or current during the hybridization; and
   c) determining whether or not the solution includes complementary nucleotide strands using the determined potential change.

2. The method of claim 1 wherein the polymer is ionically charged in its doped form.

3. The method of claim 1 wherein the ion sensitive electrode comprises polyaniline.

4. The method of claim 3 wherein the polyaniline is ionically charged in its doped form.

5. The method of claim 1 wherein the determination can distinguish a single nucleotide polymorphism.

6. The method of claim 1 wherein the probes have been immobilized onto a surface of the electrode by a covalent immobilization method.

7. The method of claim 6 wherein the covalent immobilization method is selected from a group consisting of (A) thiol addition, (B) ester bond formation, and (C) amide bond formation.

8. The method of claim 1 wherein the probes have been immobilized onto a surface of the electrode by a non-covalent immobilization method.

9. The method of claim 8 wherein the non-covalent immobilization method is selected from a group consisting of (A) ink jet printing and (B) layer-by-layer deposition.

10. The method of claim 1 wherein the probes are oligonucleotide probes of length of 6-75 nucleotides.

11. The method of claim 1 wherein the act of determining a potential change includes monitored potential in an electric field created by the presence of a counter electrode.

12. The method of claim 1 wherein the probes are selected from a group consisting of (A) oligonucleotides, (B) polymerase chain reaction, (C) genomic DNAs, (D) bacterial artificial chromosomes, and (E) plasmids.

13. Apparatus comprising means for detecting or measuring nucleotide strand hybridization comprising:
   a) an ion sensitive electrode to be provided in solution, wherein the ion sensitive electrode comprises an electrically conducting polymer and probes comprising nucleotide strands;

b) means for determining a potential change in the solution without applying any external voltage or current during the hybridization; and
c) means for determining whether or not the solution includes complementary nucleotide strands using the determined potential change.

14. The apparatus of claim 13 wherein the ion sensitive electrode comprises polyaniline.

15. The apparatus of claim 13 wherein the means for determining can distinguish a single nucleotide polymorphism.

16. The apparatus of claim 13 wherein the probes have been immobilized onto a surface of the electrode by a covalent immobilization method.

17. The apparatus of claim 13 wherein the probes have been immobilized onto a surface of the electrode by a non-covalent immobilization method.

18. The apparatus of claim 13 wherein the probes are oligonucleotide probes of length of 6-75 nucleotides.

19. The method of claim 13 wherein the probes are selected from a group consisting of (A) oligonucleotides, (B) polymerase chain reaction, (C) genomic DNAs, (D) bacterial artificial chromosomes, and (E) plasmids.

20. The method of claim 1 wherein the act of determining a potential change in the solution is done without applying an externally sourced voltage or current after the hybridization.

21. The apparatus of claim 13 wherein the means for determining a potential change in the solution does so without applying any external voltage or current after the hybridization.

22. The method of claim 1 wherein the electrically conducting polymer is an organic conducting polymer.

23. The apparatus of claim 13 wherein the electrically conducting polymer is an organic conducting polymer.

* * * * *